(12) United States Patent
Milanese et al.

(10) Patent No.: US 8,791,269 B2
(45) Date of Patent: Jul. 29, 2014

(54) COMPLEX OF AMORPHOUS TOMOXIPROLE AND CYCLODEXTRIN WITH FAST DISSOLUTION RATE AND PROCESS FOR THE PREPARATION THEREOF

(75) Inventors: Alberto Milanese, Monza (IT); Marino Nebuloni, Rho (IT); Lucia Carrano, Legnano (IT)

(73) Assignees: Fondazione Istituto Insubrico di Ricerca per la Vita, Gerenzano (IT); Fondazione Cariplo, Milan (IT)

( * ) Notice: Subject to any disclaimer, the term of this patent is extended or adjusted under 35 U.S.C. 154(b) by 0 days.

(21) Appl. No.: 14/125,468

(22) PCT Filed: Jun. 14, 2012

(86) PCT No.: PCT/EP2012/061261
§ 371 (c)(1),
(2), (4) Date: Jan. 17, 2014

(87) PCT Pub. No.: WO2013/004462
PCT Pub. Date: Jan. 10, 2013

(65) Prior Publication Data
US 2014/0128343 A1    May 8, 2014

(30) Foreign Application Priority Data

Jul. 1, 2011 (IT) .............................. MI2011A1235

(51) Int. Cl.
| | |
|---|---|
| *C07D 215/18* | (2006.01) |
| *C08B 37/16* | (2006.01) |
| *A61K 47/48* | (2006.01) |
| *C07D 235/02* | (2006.01) |
| *A61K 9/00* | (2006.01) |

(52) U.S. Cl.
CPC .......... *C08B 37/0015* (2013.01); *C07D 215/18* (2013.01); *A61K 47/48969* (2013.01); *C07D 235/02* (2013.01); *A61K 9/0053* (2013.01)
USPC ...................................... 548/302.1; 514/394

(58) Field of Classification Search
None
See application file for complete search history.

(56) References Cited

FOREIGN PATENT DOCUMENTS

EP    1219306    7/2002

OTHER PUBLICATIONS

Rajewski, R.A., et al., Pharmaceutical Applications of Cyclodextrins. 2..., Journal of Pharmaceutical Sciences, American Pharmaceutical Assoc., vol. 85, No. 11, pp. 1142-1169, 1996.
Loftsson, T., Pharmaceutical Applications of Cyclodextrins. 1..., Journal of Pharmaceutical Sciences, vol. 85, No. 10, pp. 1017-1025, 1996.
Bernareggi, A., et al., High-Performance Liquid Chromatography..., Journal of Liquid Chromatography, vol. 7, No. 10, pp. 2093-2101, 1984.
Challa, R., et al., Cyclodextrins in Drug Delivery..., AAPS Pharmscitech, vol. 6, No. 2, pp. E329-E357, 2005.
Rajewski, R.A., et al., Pharmaceutical Applications of Cyclodextrins..., Journal of Pharmaceutical Sciences, American Pharmaceutical Assoc., vol. 85, No. 11, pp. 1142-1169, 1996 (Abstract).
Mihajlovic, T., et al., Improvement of Aripiprazole Solubility by Complexation..., AAPS Pharmscitech, vol. 13, No. 2, pp. 623-631, 2012.
International Search Report issued in counterpart PCT Application No. PCT/EP2012/061261, (2012).
International Preliminary Report on Patentability issued in counterpart PCT Application No. PCT/EP2012/061261, (2014).

*Primary Examiner* — Eric Olson
(74) *Attorney, Agent, or Firm* — Silvia Salvadori, P.C.

(57) ABSTRACT

A stable complex of tomoxiprole with 2-hydroxypropyl-beta-cyclodextrin with fast dissolution rate and rapid absorption wherein amorphous tomoxiprole forms a complex with 2-hydroxypropyl-beta-cyclodextrin in about equimolecular ratio. The complex shows a remarkably faster dissolution rate and absorption with respect to crystalline tomoxiprole and is particularly suitable for the production of pharmaceutical oral dosage forms, such as tablets and capsules, where rapid onset of therapeutical action is required. A method of manufacture of the complex is also described and claimed.

12 Claims, 6 Drawing Sheets

COMPLEX OF AMORPHOUS TOMOXIPROLE AND CYCLODEXTRIN WITH FAST DISSOLUTION RATE AND PROCESS FOR THE PREPARATION THEREOF

This application is a U.S. national stage of PCT/EP2012/061261 filed on Jun. 14, 2012, which claims priority to and the benefit of Italian Application No. MI2011A001235 filed on Jul. 1, 2011, the contents of which are incorporated herein by reference in their entirety.

TECHNOLOGICAL BACKGROUND

Tomoxiprole, 2-(4-methoxyphenyl)-3-(1-methylethyl)-3H-naphth[1,2-d] imidazole (formerly indicated as MDL 035) is a compound belonging to the class of the cycloxygenase 2 inhibitors, with analgesic, antinflammatoriry, antiarthritis activity The efficacy of tomoxiprole against said disorders has been demonstrated in animal studies. In contrast to most clinically used drugs, active doses of the compound are devoid of ulcerogenic activity (P. Schiatti et al. *Arzneim-Forsch/Drug Res* 1986, 36, 102-109; See also EP 0 012 866 A1)

Figure 1:
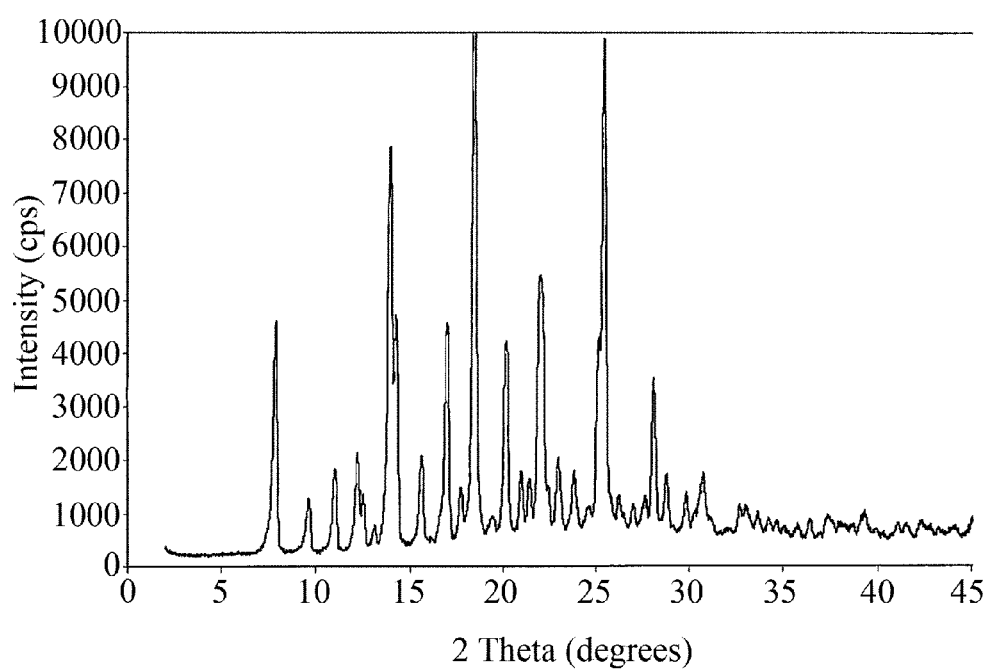

Pharmacokinetics studies demonstrated that a substantial percentage of the tomoxiprole orally administered is absorbed and gives adequate concentrations in the blood lasting several hours. However the absorption is slow, attaining the maximum concentration of the substance in the blood over one hour after administration (A. Bernareggi et al. *J. Liquid Chromatography* 1984, 7, 2093-2101). Due to its high lipophilicity tomoxiprole unless ionized is practically insoluble in water. It is a weak base: at pH values lower than 2 is partially ionized and moderately soluble in water. The rate of dissolution is slow, due to physical properties of the crystal form (Form I) in which the compound has been so far obtained. The XRPD of the crystals are shown in FIG. 1.

Since the molecule exhibits good membrane permeation characteristics, its slow solution rate in gastric fluids appears to be responsible for its slow absorption and consequently of a delayed onset of action.

The main predicted use of tomoxiprole is as analgesic, for the management of diseases as dental pain, post traumatic pain, headache and dysmenorrhoea. A rapid onset of the therapeutical action with consequent relieve of the pain is an important aspect of the medical treatment of said diseases.

The present invention relates to different approaches to obtain a faster solution rate of the molecule in conditions mimicking gastric juice, and hence a more rapid absorption of the drug.

First Approach: Amorphous Form or Novel Crystal Forms

The slow dissolution rate of tomoxiprole Form I crystals (illustrated in FIG. 2) is due to their physical characteristics: low surface wettability (water contact angle 81° at any pH) and a high crystal lattice stability, as demonstrated by the melting point (165° C.). Attempts at obtaining different crystal forms consisting in dissolving the sample in a solvent and inducing precipitation by cooling or concentrating the solution failed. Several solvents were used, such as acetone, anhydrous ethanol, methylene chloride. In all the cases the crystal Form I, melting point 165° C., (determined by DSC, see graph reported in FIG. 5) was observed.

Surprisingly, whereas from anhydrous ethanol Form I crystallized, from ethanol 96% a solid mainly consisting of a new form (Form II) was obtained. Pure crystals of the new form were prepared by dissolving the sample in methanol, adding water to precipitate the compound and removing methanol under vacuum. Form II in DSC is characterized by a melting point 155° C., followed by recrystallization into Form I and subsequent melting at 165° C. As predicted by the DSC results, Form II is unstable and even at room temperature slowly transforms into Form I.

It is a common knowledge that the amorphous form of a product have a dissolution rate much faster than that of crystal structure. This is due to the fact that amorphous forms have larger surface area and their lattice energy is much weaker than in crystals. Said factors influence the dissolution rate but not the absolute solubility of the different physical structures, which depends on other factors, mainly the ionization degree of the substance.

Attempts of preparing the amorphous form were performed by dissolving the sample in a solvent and obtaining a rapid precipitation by slow addition of a solvent in which tomoxiprole is not soluble. By addition of water to ethanol or acetone solutions, or of petroleum ether to chloroform or dichlorometane solutions, crystals of Form I were always produced. By dissolving tomoxiprole in methanol and addition of water the above described crystals of Form II were obtained.

The only positive result, formation of an amorphous form, was obtained by a different technique, consisting of the instant evaporation of a tomoxiprole solution. A solution of tomoxiprole in ethanol was flash evaporated by spray drying. A vitreous amorphous layer of tomoxiprole was obtained. However, the substance was highly instable and in a short time transformed into Form I crystals. Hence it appears that the amorphous form of the compound is intrinsically unstable.

Second Approach: Complexes of Tomoxiprole with Cyclodextrins

Scientific literature and patents report many examples of increasing the water solubility of drugs by forming complexes or adducts of compounds with cyclodextrins. However, in general, significantly enhanced solubility is obtained only with high molar ratios cyclodextrin/active substance. In many examples, solutions of over 10% (wt/vol) of cyclodextrin are used to obtain a significant solubility of the drug (T. Loftsson et al. *J. Pharm. Sc.* 1996, 85, 1017-1025). Said drug/cyclodextrin ratios are suitable for parenteral administration or acqueus eye drops but the high relative amount of cyclodextrin respect to drug makes these technically unsuitable for the preparation of tablet or capsules for oral administration.

In industrial pharmaceutical practice and in commercial use, including patients compliance, limits are imposed to the size of orally delivering devices. In general, the total content of active ingredients of a tablet or capsule, preferably, should not exceed the weight of one gram.

Another reported property of drug/cyclodextrin complexes is stabilization of the active product crystalline or amorphous solid state forms.

However, the state of the art shows that in most cases the stabilization of an amorphous form of a substance is obtained with a molar ratio cyclodestin/substance higher than 2. As an example in US 2006/0135473 is reported that the complex beta-cyclodextrin/piroxicam with molar ratio 2.5:1 shows the best stabilization and dissolution rate performance.

Another teaching derivable from the state of the art is that in several cases it is not possible to obtain a substance/cyclodextrin adducts were the substance is totally present in amorphous form (M. N. Reddy et al. *AAPS J.* 2004, 6, 68-86; S. Rawat et al. *Eur. J. Pha.r Biopharm.* 2004, 57, 263-267). For instance, in said documents it is shown that several different methods of preparing a celecoxib/beta-cyclodextrin complex yielded only mixtures of crystalline celecoxib and amorphous adducts. Moreover, not always the formation of a complex of active substance/cyclodextrin stabilizes the amorphous form of the active substance (F. Hirayama et al. *Pharm. Res.* 1994, 11, 1776-70, PubMed 7899242). In this document it is disclosed that the complex nifedipine/2-hydroxypropyl-beta-cyclodextrin, rather than to stabilize the substance in its amorphous form, accelerates its conversion to a crystalline form. EP 1219306 A discloses compositions comprising cyclodextrins and NO-releasing drugs where the drug is bound to a NO-releasing radical.

Although tomoxiprole is mentioned among an extremely large group of compounds which may be bound to a NO-releasing radical and then combined with cyclodextrin, this document does not contain any disclosure of a complex and a method for the preparation thereof where the molar ratio between the active substance and cyclodextrin has a predetermined value and does not provide any indication or hint or suggestion to preparing a stable complex where tomoxiprole is contained in a molar ratio near 1:1 with 2-hydroxypropyl-beta-cyclodextrin.

DESCRIPTION OF THE INVENTION

This invention relates to the preparation of a stable amorphous tomoxiprole-cyclodextrin complex with molar ratio near 1:1, presenting a fast dissolution rate at acidic pH. In particular, this invention concerns the preparation and use of a complex in which amorphous tomoxiprole is stabilized by forming a complex with an about equimolecular amount of 2-hydroxypropyl-beta-cyclodextrin, suitable for preparing devices for oral administration, such as tablet or capsules, and presenting a dissolution rate in an aqueous solution buffered at acidic pH which is remarkably faster than that of tomoxiprole crystalline Form I.

Experiments for the preparation of complexes have been performed with various cyclodextrins according to known techniques or introducing rational modification on the basis of previous results. After several failed attempts, a method described in detail hereafter, was devised by which a stable amorphous complex of tomoxiprole with 2-hydroxypropyl-beta-cyclodextrin was obtained.

In general molar ratios 1:1 to 1.5 of the reactants were dissolved in solvents such as alcohols, pyridine, tetrahydrofuran, butanol, either alone or in mixture with water. By evaporation of the solvent and cooling, solids of various compositions were obtained. Thin layer chromatography was used to analyze the products composition: using a suitable eluent free tomoxiprole was revealed by the presence of a spot, fluorescent under UV light, migrating near the front of the solvent. The presence of a complex was revealed by a fluorescent spot remaining with the cyclodextrin on the starting line of the chromatography. The percentage of tomoxiprole, in the mixtures or in the complexes was determined by quantitative UV analysis.

Several experiments were performed by reacting 2-hydroxypropyl-beta-cyclodextrin with tomoxiprole in mixtures of solvents in different conditions. The results were generally unsatisfactory. TLC analysis revealed that some of the products were mixtures of cyclodextrin and microcrystals of tomoxiprole, or other amorphous mixtures of cyclodextrin and tomoxiprole. A few appeared as composed by cyclodextrin containing a little amount of the desired complex.

A common practice for the preparation of complexes substance/cyclodextrin, consists of dissolving the two components in a suitable solvent or mixture of solvents and then concentrating the solution by evaporation at reduced pressure. An explanation of the failures of the attempts above mentioned could be that tomoxiprole is generally less soluble than 2-hydroxypropyl-beta-cyclodextrin in polar solvents. Concentration at reduced pressure substantially lowers the temperature of the solution causing the partial precipitation of tomoxiprole. Therefore, a method has been devised to rapidly evaporate the solvents without cooling the solution.

TMX/HPBCP: tomoxiprole-2-hydroxypropyl-beta-cyclodextrin complex

According to the method of the invention tomoxiprole and 2-hydroxypropyl-beta-cyclodextrin (HPBCD) in molar ratios ranging from 1:1 to 1:1.5 are added to ethanol and the mixture is heated at 30-40° C. to obtain a clear solution which is then rapidly evaporated at atmospheric pressure under a warm air stream (40-50° C.), till an amorphous solid is formed. The products of the different preparations are collected and dried under vacuum. The content of tomoxiprole in the samples, as determined by the UV light extinction at 328 nm is in the range of 17% to 17.5% by weight. In the complex tomoxiprole/HYPBCD with molar ratio 1:1 the calculated content of tomoxiprole is 18.6% by weight. Therefore, the samples appear to be constituted by the said complex with a purity degree in the range from 90 to 93% (by weight). Further washing of the obtained product with a solvent capable of removing unreacted cyclodextrin yields a complex wherein the ratio is near 1:1 as shown in Example 1. The complex shows a remarkably faster dissolution rate in comparison with tomoxiprole crystals Form 1.

Figure 2:
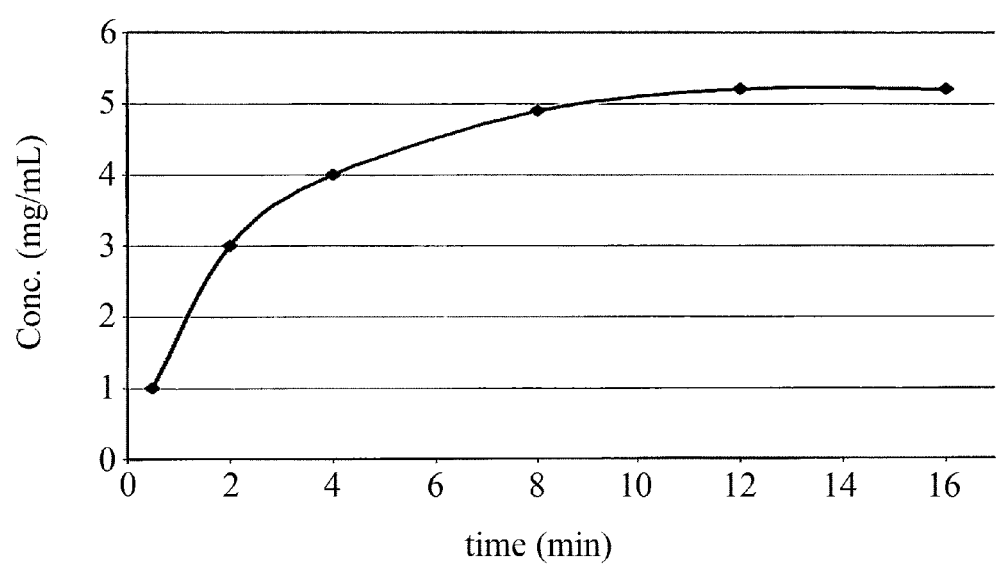
Figure 6:
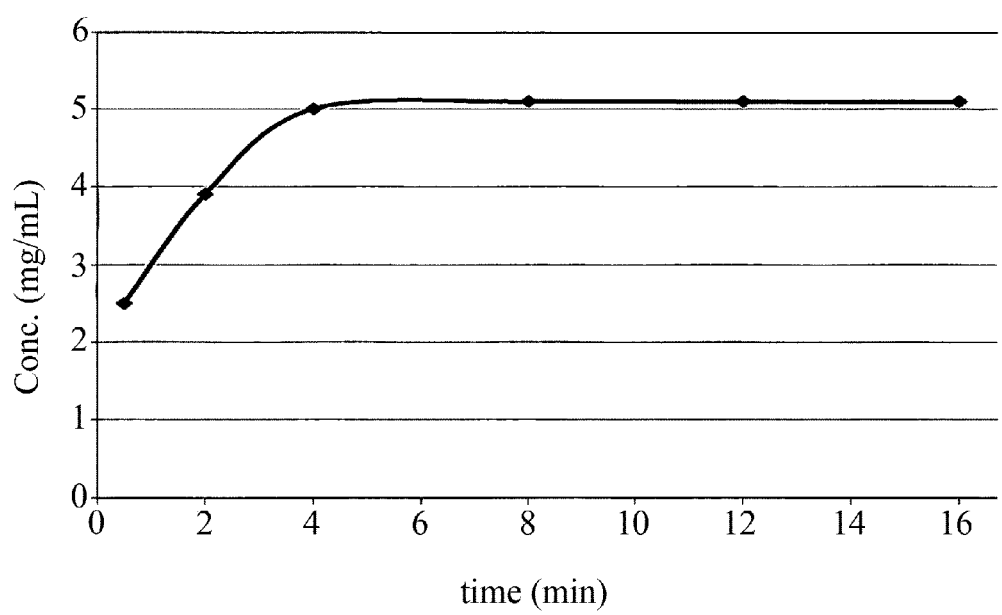

The dissolution rate of tomoxiprole crystals Form 1 and the complex are illustrated in FIG. 2 and FIG. 6, respectively.

In the following Table 1 are reported the concentrations of the substances at the different times obtained with the method described in Example 2, the results of which are represented in FIG. 2 and FIG. 6.

TABLE 1

Dissolution rate of tomoxiprole crystals and complex tomoxiprole/HPBCD

| Substance (mg/mL dissolved) | Time (min) | | | | | | |
|---|---|---|---|---|---|---|---|
| | 0.5 | 2 | 4 | 6 | 8 | 10 | 12 |
| Tomoxiprole crystals | 1 | 3 | 4 | — | 4.9 | — | 5.2 |
| Complex tomoxiprole/HPBDCD | 2.5 | 4 | 5 | — | 5.1 | — | 5.1 |

The saturation concentration at the conditions reported in Example 2 is about 5 mg/ml.

The concentration observed with the complex at 0.5 min. is 2.5 mg/mL, or 50% of the total soluble amount. The concentration determined at the same time with tomoxipole crystals is 1 mg/mL or 20% of the soluble amount. The saturation concentration is reached after 4 min with the complex and over 8 min with tomoxiprole crystals.

To assess whether the faster dissolution rate observed for the complex actually corresponds to a faster in vivo absorption, the pharmacokinetic behaviour of tomoxiprole (TMX) and tomoxiprole-2-hydroxypropyl-beta-cyclodextrin complex (TMX/HPBCD) in rats have been compared.

Experimental design: Two groups of four rats each have been used. To the rats of each group was orally given either a dose of 5 mg/Kg of tomoxiprole or a dose of complex tomoxiprole-2-hydroxypropyl-beta-ciclodestrin corresponding to 5 mg/Kg of active substance. The test compounds have been administered as a suspension in 0.5% methocel (K15, The Dow Chemical Co.) prepared immediately before administration. Samples of blood were collected at 0.3, 0.6, 1, 1.5, 2 and 6 hours, and plasma separated by centrifugation. Sample processing and HPLC analyses were performed as previously described (A. Bernareggi et al. *J. liquid chromatography* 1984, 7, 2093-2101). The pharmacokinetic parameters calculated from the plasma levels of tomoxiprole observed with the two formulations are reported in the following Table 2

TABLE 2

Comparison of pharmacokinetic behaviour of tomoxiprole and complex tomoxiprole-2-hydroxypropyl-beta-cyclodextrin (TMX/HPBCD)

| Formulation | Tmax (min) | Cmax (mg/L) | $AUC_{(20\text{-}40\ min)}$ (mg · h/L) | $AUC_{(0\text{-}6\ h)}$ (mg · h/L) |
|---|---|---|---|---|
| TMX | 90 | 0.22 | 0.046 | 1.17 |
| TMX/HPBCD | 40 | 0.36 | 0.118 | 1.23 |

The faster absorption of the complexed tomoxiprole is demonstrated by the maximum haematic concentration, 0.36 mg/L at 40 min against the maximum haematic concentration (Cmax) observed with tomoxiprole crystals, 0.22 mg/L at 90 min. Moreover, as demonstrated by the values of $AUC_{(20\text{-}40min)}$ (area under the curve from 20 to 40 min), the absorption of the complex in the interval 20-40 min is 0.118 mg·h/L that is 2.55 times that of tomoxiprole crystals (0.046 mg·h/L).

As expected, there is no significant difference in the total amount absorbed in plasma with the two formulations, as demonstrated by the $AUC_{(0\text{-}6h)}$ (area under the curve from 0 to 6 h, 1.17 mg·h/L and 1.23 mg·h/L respectively).

The complex of amorphous tomoxiprole with 2-hydroxypropyl-beta-cyclodextrin, according to this invention is very stable: after six months of storage at room temperature no signs of formation of tomoxiprole crystals were detected.

The complex is particularly suitable for the preparation according to methods known in the art of pharmaceutical oral dosage forms, such as tablets and capsules, especially for use in the treatment of patients needing rapid absorption of tomoxiprole and onset of the therapeutical action.

According to a preferred embodiment of this invention, oral dosage units, such as tablets and capsules, are provided, each of which having a content of the complex of amorphous tomoxiprole with 2-hydroxypropyl-beta-cyclodextrin herein described which corresponds to from 50 to 150 milligrams of tomoxiprole.

EXAMPLES

Example 1

Tomoxiprole-2-hydroxypropyl-beta-cyclodextrin Complex 4 g of tomoxiprole (12 mMol) (Mw 316.4) and 21 g of 2-hydroxypropyl-beta-cyclodextrin (15 mMol) (Aldrich Chemical Company, average MW 1380) are dissolved in 150 ml of ethanol. The solution is heated at 30-40° C. for 30 minutes to obtain a clear solution and then rapidly evaporated at atmospheric pressure under a warm air stream at 40-50° C. until a solid residue is formed. The product, dried under vacuum at 60° C., appears as an amorphous powder. The XRPD pattern (FIG. 3) confirms the essentially amorphous form of the sample with a few traces of tomoxiprole crystals. The infrared spectrum of the product (FIG. 4B) is in agreement with the assumption that the product is essentially an equimolecular inclusion complex of tomoxiprole and 2-hydroxypropyl-beta-cyclodextrin, mixed with some unreacted cyclodextrin. The content of tomoxiprole in the sample is about 17% by weight. The content calculated for an equimolecular complex is 18.8%. This indicates that the product is by 90% (by weight) composed of the equimolecular complex and by about 10% of unreacted cyclodextrin. In fact elimination of cyclodextrin by washing with cold ethanol yields an almost pure complex with a tomoxiprole titer of about 18.5% corresponding to a molar ratio tomoxiprole/cyclodextrin of near 1:1.

In Table 3 are reported the most characteristic infrared absorption bands of the complex tomoxiprole-2-hydroxypropyl-beta-cyclodextrin in comparison with those of tomoxiprole.

TABLE 3

Characteristic infrared absorption bands of tomoxiprole and tomoxiprole-2-hydroxypropyl-beta-cyclodextrin complex

| attribution | TMX $cm^{-1}$ | TMX/HPBCD $cm^{-1}$ |
|---|---|---|
| arom. ν CH | 2964 | 3343 |
| asym. ν CH3 | | |
| sym. ν (O—)CH3 | 2839 | 2927 |
| | 1607 | 1609 |
| ν C=N and ν C=C | 1575 | |
| | 1526 | 1526 |
| δ asym. CH3 | 1457 | 1457 |
| | 1439 | |
| | 1420 | |
| δ sym. CH3 | 1392 | 1370 |
| | 1361 | |
| | 1309 | |
| | 1293 | |
| ν asym C—O—C | 1248 | 1250 |
| | 1179 | 1150 |
| | 1117 | |
| ν sym C—O—C | 1050 | 1081 |
| | 1019 | 1020 |
| arom γ CH | 837 | 947 |
| | 801 | 838 |
| | 738 | 801 |
| | 718 | 752 |
| | 699 | 700 |
| | 613 | |
| | 575 | |
| | 524 | 575 |
| | | 521 |

Experimental conditions
The FT-IR spectra were recorded at the solid state by the Perkin Elmer - Spectrum Two instrument, scan range 4500-400 $cm^{-1}$ resolution 4 $cm^{-1}$
TMX: tomoxiprole
HPBCD: 2-hydroxypropyl-beta-cyclodextrin
TMX/HPBCP: tomoxiprole-2-hydrozypropyl-beta-cyclodextrin complex In TMX/HPBCD complex the absorption bands characteristic of TMX are not detected confirming that the original crystals of TMX are not present.

In addition, the new bands at 2927, 1250 and 1150 $cm^{-1}$, not remarkably present in the TMX spectrum, confirm the presence of hydrogen bonds operative between the HPBCD and TMX.

Example 2

Tomoxiprole-2-hydroxypropyl-beta-cyclodextrin Complex Dissolution Rate

The dissolution rate of the complex tomoxiprole-2-hydroxypropyl-beta-cyclodextrin obtained in Example 1 is determined by the following method.

In a flask provided with magnetic mixer 600 mg of tomoxiprole-2-hydroxypropyl-beta-cyclodextrin complex (corresponding to 100 mg of tomoxiprole) are added to 10 ml of a buffer solution HCl—KCl pH 1.5. Samples of the suspension are collected at intervals of time, clarified by centrifugation and the tomoxiprole concentration in the clear supernatant is determined by UV absorption at 328 nm.

The dissolution rate of tomoxiprole crystals was measured for comparison purpose. The method was the same of that described above, with the exception that 100 mg of tomoxiprole were added instead of 600 mg of complex tomoxiprole/HPBCD The results are illustrated in FIG. 6 and FIG. 2, respectively.

Quantitative differences of the results illustrated in said figures are reported in Table 1 and confirm a faster dissolution rate of the complex as compared with that of tomoxiprole crystals Form I)

DRAWINGS

FIG. 1: XRPD pattern of tomoxiprole crystals Form I.
The X-rays powder diffraction (XRPD) test was carried out with MINIFLEX (Rigaku) instrument; the tube has a Copper target, with a current intensity of 15 mA and a voltage of 30 kV: the radiation was constituted by $K_{\alpha 1}$ (1.540562 Å) and $K_{\alpha 2}$ (1.544398 Å); Nickel filter was used for the suppression of $K_\beta$ radiation (1.392218 Å).
Vertical axis: Intensity (cps); horizontal axis: 2-theta in degrees.

FIG. 2: Dissolution rate of tomoxiprole in buffer pH 1.5; Vertical axis: concentration of tomoxiprole (mg/mL); horizontal axis: time (minutes).

Figure 3:
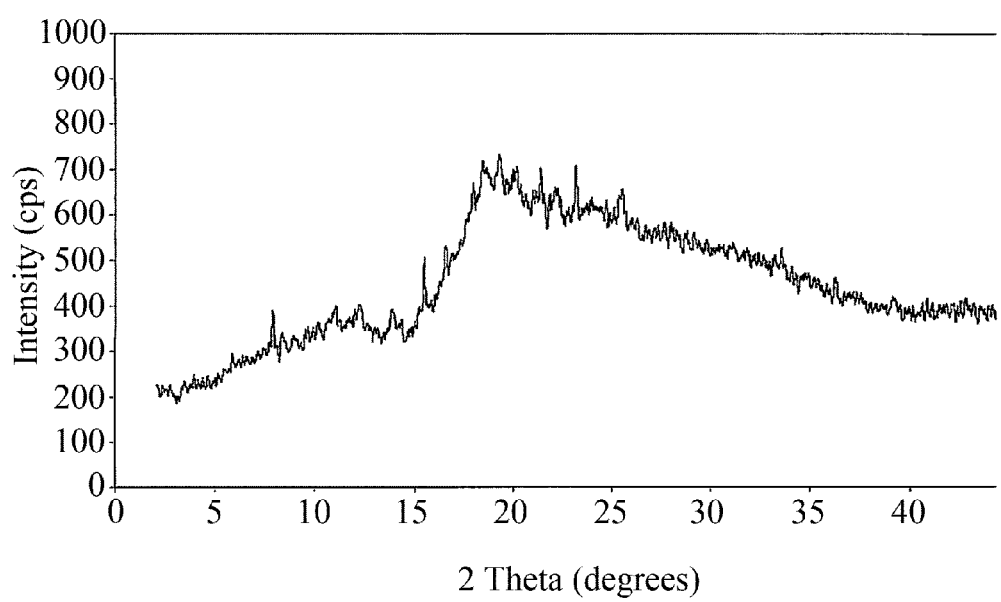

FIG. 3: XRPD pattern of the complex tomoxiprole-2-hydroxypropyl-beta-cyclodextrin;
The X-rays powder diffraction (XRPD) test was carried out with MINIFLEX (Rigaku) instrument; the tube has a Copper target, with a current intensity of 15 mA and a voltage of 30 kV: the radiation was constituted by $K_{\alpha 1}$ (1.540562 Å) and $K_{\alpha 2}$ (1.544398 Å); Nickel filter was used for the suppression of $K_\beta$ radiation (1.392218 Å).
Vertical axis: Intensity (cps); horizontal axis: 2-theta in degrees.

Figure 4A:
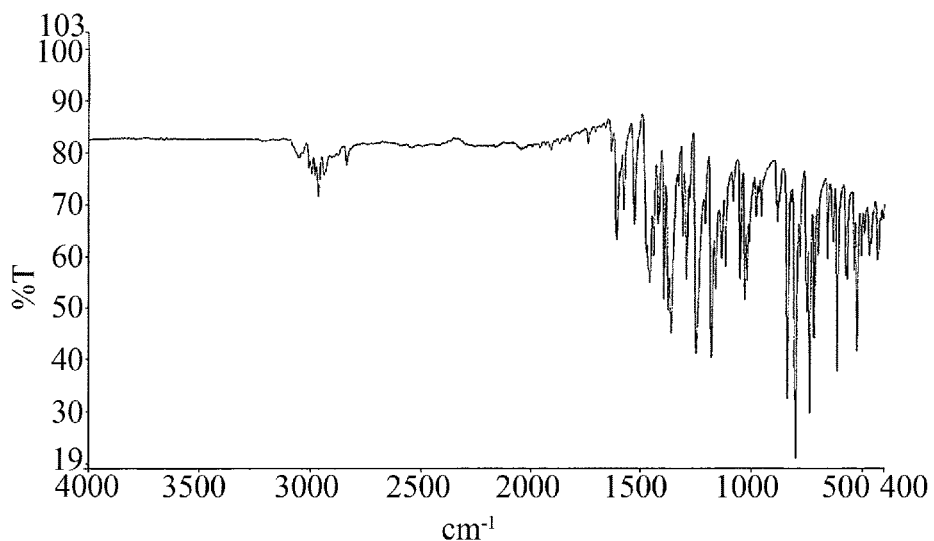
Figure 4B:
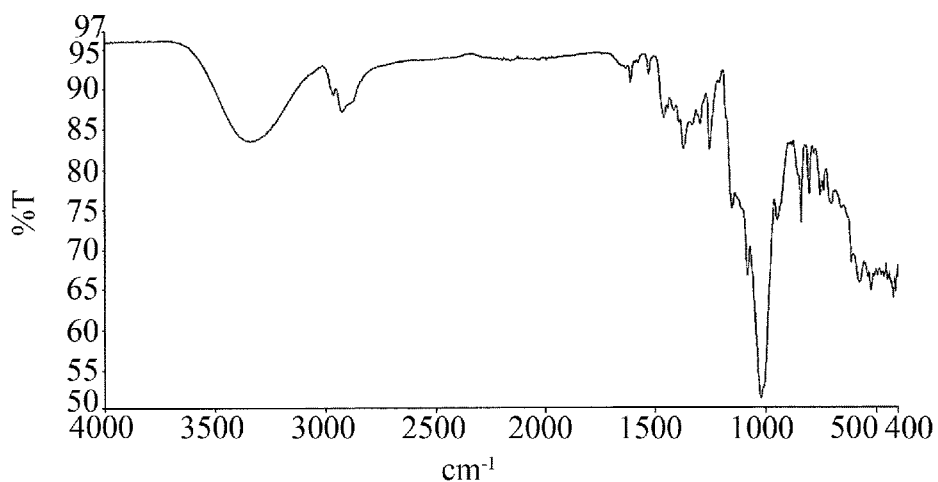

FIGS. 4A and 4B: Infrared spectrum of tomoxiprole and complex tomoxiprole-2-hydroxypropyl-beta-cyclodextrin;.
Vertical axis: % transmission (% T); horizontal axis: frequency (cm$^{-1}$)
The methods and the conditions employed are reported under Table 2. Relevant commentes are also reported under the same Table.

Figure 5:
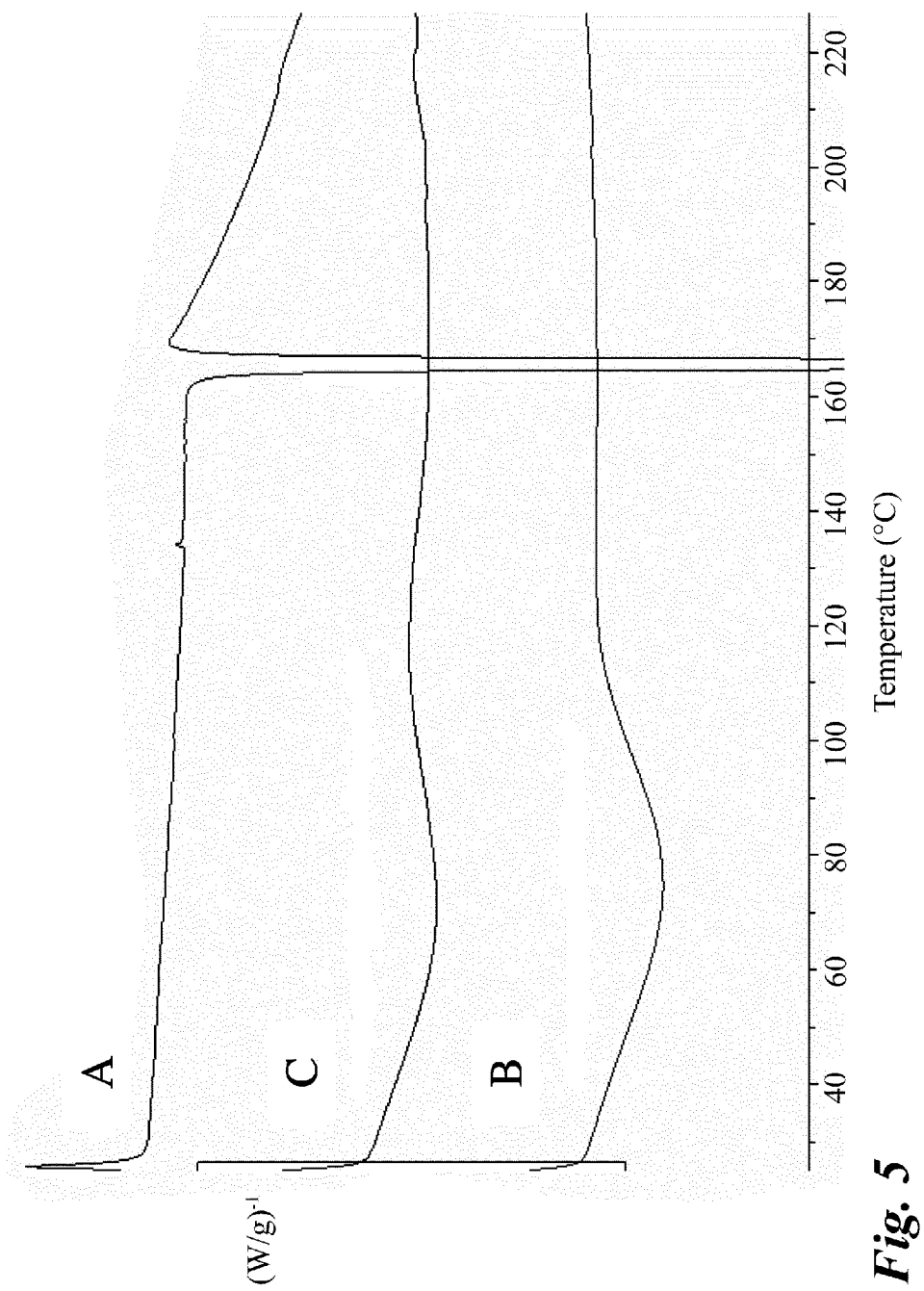

FIG. 5: Differential Scanning Calorimetry plot of tomoxiprole, 2-hydroxypropyl-beta-cyclodextrin and complex tomoxiprole-2-hydroxypropyl-beta-cyclodextrin.
The Differential Scanning Calorimetry (DSC) was carried out with DSC 821 (Mettler-Toledo) lying the samples in an open, covered, aluminum pan. The heating rate was set at 10° C./min, under nitrogen flow at 30 ml/min.
Vertical axis: (W/g)$^{-1}$; horizontal axis: temperature (° C.).

FIG. 5A—thermal behaviour of tomoxiprole. A sharp absorption of energy is observed at 165.-167° C., due to the melting of tomoxiprole crystals FIG. 5B—thermal behaviour of 2-hydroxypropy-beta-cyclodextrin. A gradual energy absorption is observed from room temperature until 120° C. corresponding to a desolvation endotherm FIG. 5C—thermal behavior of the complex tomoxiprole-2-hydroxypropyl-beta-cyclodextrin. A desolvation endotherm is observed from room temperature until 130° C. No peak related to tomoxiprole is detected demonstrating that this substance is linked in amorphous form to the matrix.

FIG. 6: Dissolution rate of the complex tomoxiprole-2-hydroxypropyl-beta-cyclodextrin.
Vertical axis: concentration of tomoxiprole (mg/mL); horizontal axis:time (min)
For a quantitative comparison with tomoxiprole dissolution time see Table 1.

The invention claimed is:

1. A complex of tomoxiprole with 2-hydroxypropyl-beta-cyclodextrin wherein tomoxiprole is stabilized in amorphous form and the molar ratio between the amorphous tomoxiprole and 2-hydroxypropyl-beta-cyclodextrin ranges from 0.9:1 and 1:1.

2. A complex according to claim 1, which is a complex of tomoxiprole with 2-hydroxypropyl-beta-cyclodextrin wherein tomoxiprole is stabilized in the amorphous form and the content of tomoxiprole ranges from 17 to 18.5% by weight.

3. A complex according to claim 2 showing the following I.R. absorption peaks (cm$^{-1}$) 3343, 2927, 1609, 1526, 1457, 1370, 1250, 1150, 1081, 1020, 947, 838, 801, 752, 700, 575, 521.

4. A method for producing a complex of amorphous tomoxiprole with 2-hydroxypropyl-beta-cyclodextrin according to claim 1 which comprises dissolving tomoxiprole and 2-hydroxypropyl-beta-cyclodextrin in molar proportion from 1:1 to 1:1.5 in ethanol, heating the mixture at 30-40° C. to obtain a clear solution, rapidly evaporating the reaction mixture at atmospheric pressure under a warm air stream at 40-50° C. until a solid residue is formed, drying the residue under vacuum and, optionally, washing the obtained amorphous powder with cold ethanol.

5. A complex of amorphous tomoxiprole with 2-hydroxypropyl-beta-cyclodextrin according to claim 1 for use as a medicament.

6. A complex according to claim 5 wherein the medicament is an analgesic, anti-inflammatory and antiarthritic agent.

7. A pharmaceutical composition containing as active ingredient a complex of amorphous tomoxiprole with 2-hydroxypropyl-beta-cyclodextrin according to claim 1.

8. A pharmaceutical composition according to claim 7 which is a pharmaceutical oral dosage form.

9. A pharmaceutical oral dosage form according to claim 8 which is a tablet or capsule.

10. A tablet or a capsule according to claim 9 having a content of the complex of amorphous tomoxiprole with 2-hydroxypropyl-beta-cyclodextrin which corresponds to from 50 to 150 milligrams of tomoxiprole.

11. A method for treating pain which comprises administering to a patient in need thereof an effective amount of a complex of amorphous tomoxiprole with 2-hydroxypropyl-beta-cyclodextrin according to claim 1.

12. A method according to claim 11 wherein the patient needs a rapid absorption of tomoxiprole and onset of therapeutical action.

* * * * *